United States Patent [19]

Horbal et al.

[11] Patent Number: 5,249,581
[45] Date of Patent: Oct. 5, 1993

[54] PRECISION BONE ALIGNMENT

[76] Inventors: Mark T. Horbal, 2 S. Iroquois Ct. West, Warrenville, Ill. 60555; Christopher Nowacki, 1552 Chickamauga La., Long Grove, Ill. 60047

[21] Appl. No.: 731,146

[22] Filed: Jul. 15, 1991

[51] Int. Cl.[5] ............................................. A61B 5/11
[52] U.S. Cl. .................................. 128/664; 128/782; 602/1
[58] Field of Search ................. 128/68.1, 664, 665, 128/774, 781, 782

[56] References Cited

U.S. PATENT DOCUMENTS

| | | | |
|---|---|---|---|
| 4,197,855 | 4/1980 | Lewin | 128/665 |
| 4,600,012 | 7/1986 | Kohayakawa et al. | 128/665 |
| 4,670,781 | 6/1987 | Aubert et al. | 128/774 |
| 4,699,156 | 10/1987 | Gracovetsky | 128/781 |
| 4,760,851 | 8/1988 | Fraser et al. | 128/774 |
| 4,774,679 | 9/1988 | Carlin | 128/774 |
| 4,971,069 | 11/1990 | Gracovetsky | 128/781 |
| 5,022,412 | 6/1991 | Gracovetsky et al. | 128/781 |
| 5,097,839 | 3/1992 | Allen | 128/653.1 |
| 5,099,859 | 3/1992 | Bell | 128/781 |

*Primary Examiner*—Lee S. Cohen
*Assistant Examiner*—K. M. Pfaffle
*Attorney, Agent, or Firm*—Robert M. Wolters

[57] ABSTRACT

An apparatus and method for precision bone alignment includes a plurality of markers secured to bone portions prior to an orthopaedic/surgical procedure. Light emitting LED's are provided on said markers and are sensed by an optical three-dimensional sensor which provides respective positional electric signals to a computer, the computer in turn being connected to a monitor to provide a three-dimensional display. The signals prior to the orthopaedic/surgical procedure are stored in the computer. The sensor also provides signals following the orthopaedic/surgical procedure for comparison with the signals before the procedure to insure proper alignment.

17 Claims, 2 Drawing Sheets

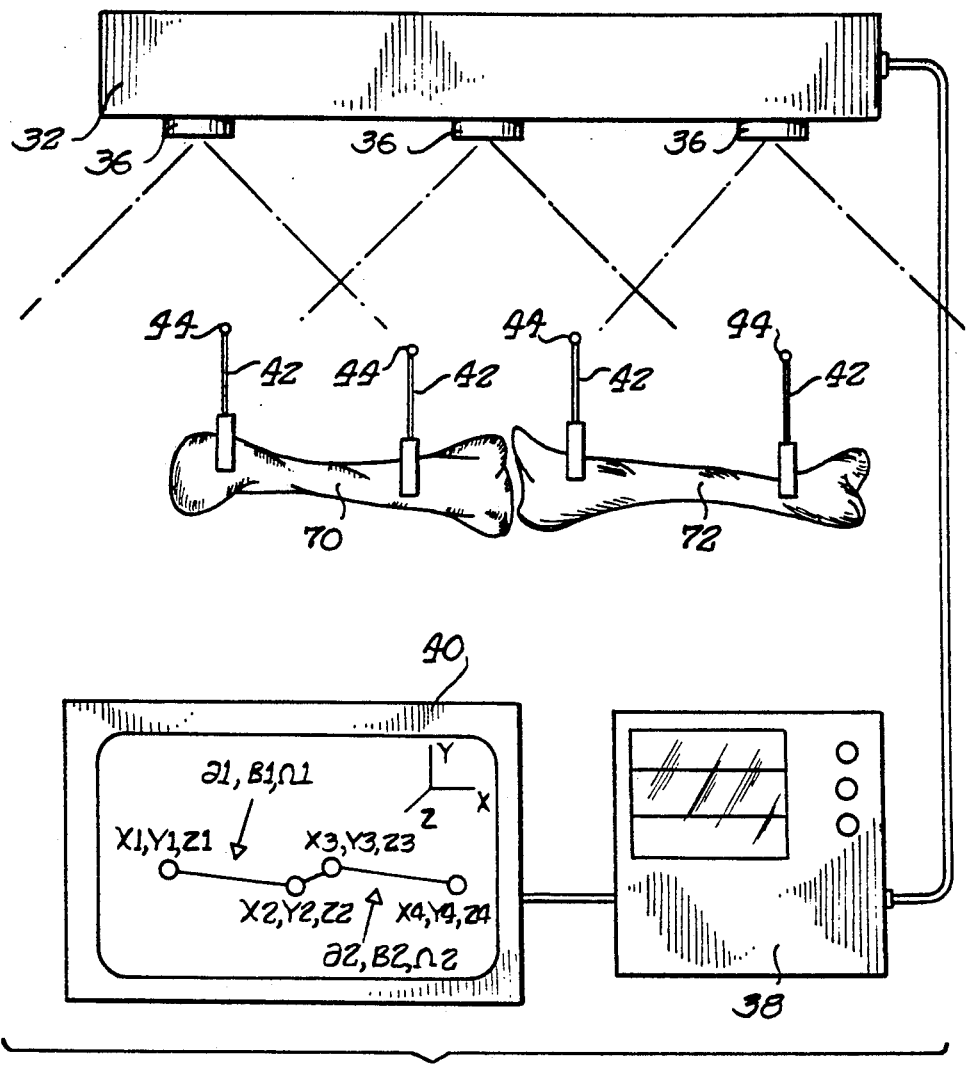
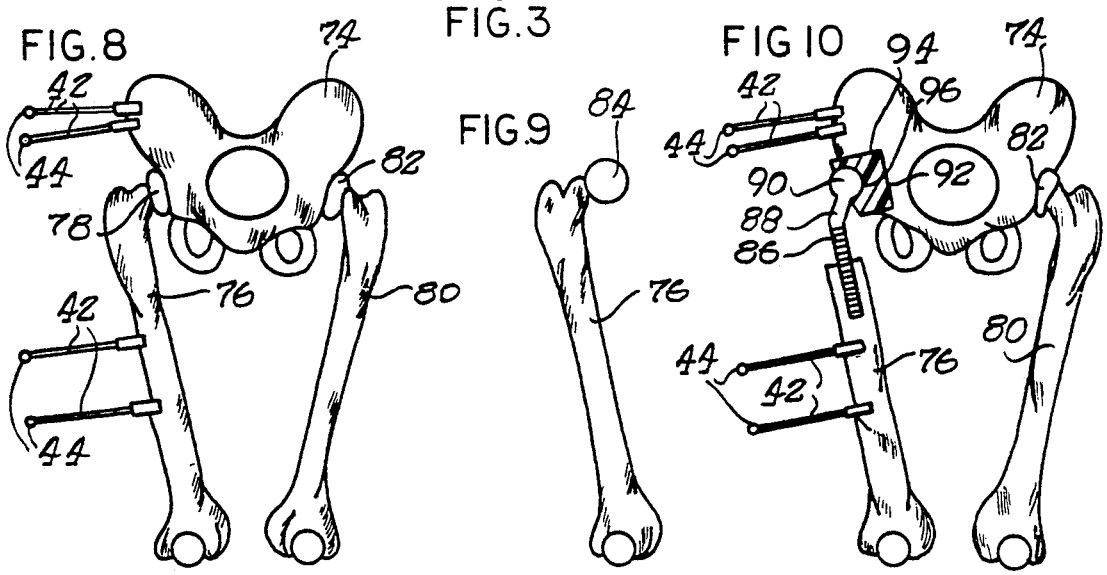

PRECISION BONE ALIGNMENT

BACKGROUND OF THE INVENTION

Modern medical practices have enabled the disabled to walk again, through the replacement of hip joints and knee joints. Obviously, for these joints to work effectively, the adjacent bones must end up in precisely the same relationship as they were in prior to the surgical replacement of the joints. Similarly, when bones are broken through accident, it is necessary to return the bone portions to their initial relative positions.

Stated otherwise, a fundamental goal of any surgical/orthopaedic procedure is full recovery. This translates to the return of maximum function to the operated area. Such optimum return requires that the post-operative physical and geometrical relationships of bones and joints in the operated area remain identical to those existing prior to the surgical treatment.

Unfortunately, the orthopaedic surgeon of today is equipped with only a few devices to aid him in performing an accurate bone alignment, and ultimate accuracy may rely on the skill and practice of the orthopaedic surgeon. Various fixators and braces are available, but are limited in application and accuracy. What is needed is something that will provide an enhanced scope of application, greater accuracy, and increased physician convenience.

Although reference has been made above to leg and hip bones and joints, it is equally applicable to arm bones, and generally speaking, the application is far broader.

OBJECTS AND SUMMARY OF THE PRESENT INVENTION

It is an object of the present invention to provide apparatus and method for precisely positioning bones or bone portions subsequent to treatment as before the treatment.

More particularly, it is an object of the present invention to provide markers secured to the bones or bone portions before a surgical/orthopaedic procedure which are observed by three dimensional sensing means to insure that the bones are returned precisely to initial relative position.

In carrying out the foregoing and other objects of the present invention, we provide a plurality of orthopaedic markers which are observed by a three dimensional sensor connected to a digital computer to provide a graphics picture available to the surgeon during the procedure.

More particularly, the orthopaedic markers are rigid fixtures made of metal or other appropriate material, rigidly mounted to the patient's bones exposed during the operative procedure. This attachment can be facilitated through the use of various clamping devices or temporary screws. Many different types of such markers can be used, depending on the surgeon's preference and the operated area. Each marker has fixed to it one or more infrared light emitting diodes (LED's). The LED's are illuminated sequentially under the control of a three dimensional sensor, such that only one LED at a time outputs a beam of infrared light.

Cooperating with the lights is a three dimensional infrared optical sensor. This sensor is somewhat akin to a stereo camera in that it has a plurality of lenses. However, the output is not one or more pictures, but rather electrical signals indicating the sensed position. The sensor is mounted on the wall or ceiling of the operating room, in some fixed position, or on a mobile cart, to provide an enhanced field of view which must cover the operating area.

The optical sensor is capable of accurately measuring and reporting the three dimensional position (X,Y,Z) of infrared LED's as noted above, mounted to the orthopaedic markers. There may be as little as one LED for each orthopaedic marker, but typically a plurality may be used. The sensor turns the LED's on and off in rapid succession, in sequence, whereby the sensor can easily differentiate between many infrared diodes.

The sensor is connected to a digital computer which receives and processes the data from the sensor. The digital computer in turn is connected to a graphics monitor which outputs the bone position and orientation data derived by the computer from the marker position data. The data is presented in a form most useful to the physician during the operation.

It should be noted that we have previously utilized infrared emitting LED's and position sensors in a quite different environment, namely in determining the precise position of a kidney stone or the like bodily concretion to be eliminated by lithotripsy, see for example our copending applications Ser. No. 07/320,110, filed Mar. 6, 1989, now abandoned, entitled, "Locating Target in Human Body", and Ser. No. 07/522,597, now abandoned, filed May 11, 1990, entitled "Locating Target in Human Body-II".

THE DRAWINGS

The present invention will best be understood from the following specification when taken in connection with the accompanying drawings wherein:

FIG. 3 is a somewhat schematic view illustrating the combination of the markers and sensor with adjacent bones, including connection through the computer to graphics monitor;

FIG. 8 is a front view of the pelvis and attached leg bones prior to hip joint replacement;

FIG. 9 is a view showing the upper leg bone or femur detached from the pelvis; and FIG. 10 shows the femur and pelvis with an inserted artificial joint, illustrating how the orthopaedic markers are returned to initial position.

DETAILED DISCLOSURE OF THE ILLUSTRATED EMBODIMENTS OF THE PRESENT INVENTION

Figure 1:
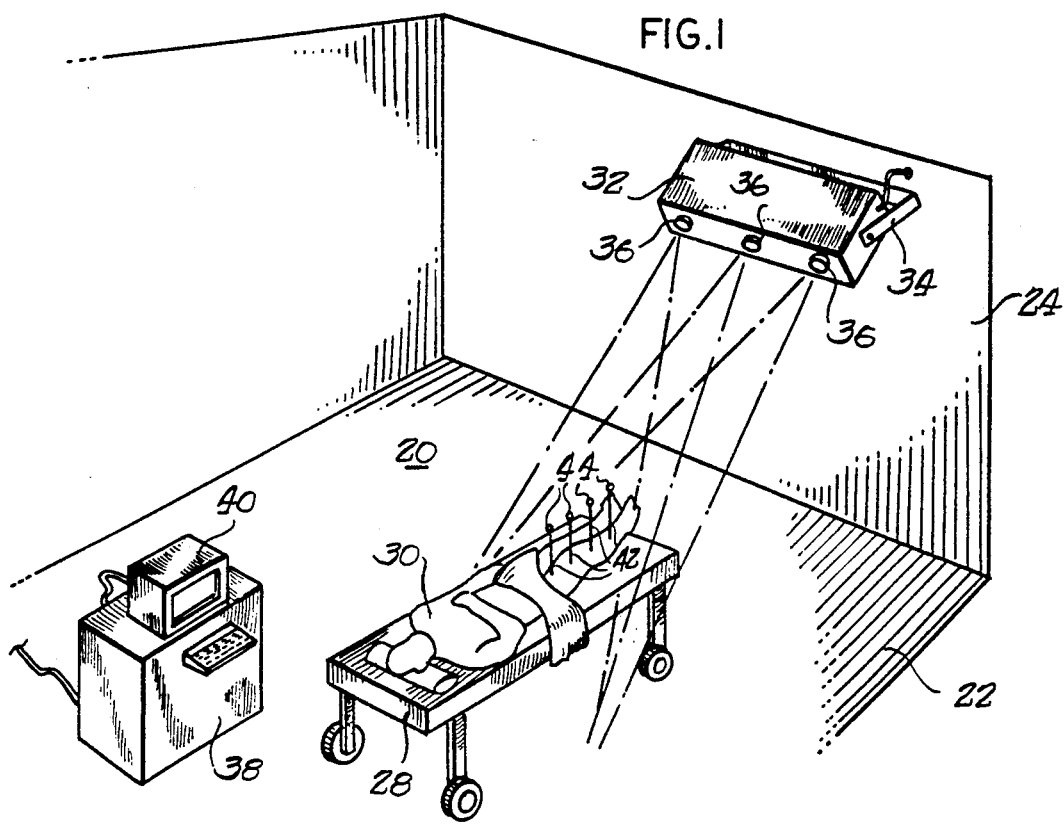
FIG. 1 is a perspective view of an operating room illustrating the apparatus and method of the present invention.
Figure 2:
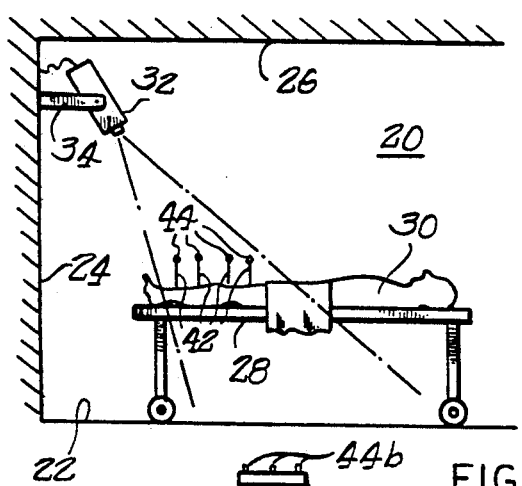
FIG. 2 is a side view partially in section and on a slightly reduced scale showing the markers and sensor of FIG. 1 as used in conjunction with a patient.

Turning now to the drawings in greater detail, and first FIG. 1 and 2, there is shown an operating room 20 comprising a floor 22, walls 24, and a ceiling 26. An operating table 28 rests on the floor 22, and a patient 30 is shown on the operating table.

A three dimensional infrared optical sensor 32 is mounted by means of a bracket 34 on one of the walls 24. It could equally well be mounted on the ceiling, or on a mobile cart. The sensor 32 comprises three cameras or sensing units in a single package, and each having a lens 36 oriented toward the operating table 28. The sensing units are available commercially, for example as the OPTOTRAK camera from Northern Digital Inc. of Waterloo, Canada. Although these devices are referred to as a "camera", this is perhaps misleading as each "camera" or sensing unit does not send out a complete picture, but rather digital information as to position of the infrared LED sensed. The center lens of the three lenses 36 is aimed straight ahead, while the two outer lenses converge in their aspect with the aspect of the center lens, being angled in at about 10°-15° toward the center. The sensor units or cameras are prefocused to provide good resolution at 1½ to 4 meters. A small computer is also housed within the housing of the optical sensor 32, and the cameras are factory calibrated with the calibration entered into the computer in the housing.

A main computer 38 rests on the floor 22, and a graphics monitor 40 is shown as disposed on top of the main computer, although it could be otherwise disposed. Four orthopaedic markers 42 are shown adjacent the patient's right leg. Specifically, two of the markers 42 are secured to the leg bone above the knee, while two are secured to the leg bone beneath the knee. Each orthopaedic marker carries an infrared LED 44 in fixed relation to the marker at the upper end thereof. There may be one such LED per marker, or there may be a plurality. Wires connecting the LED's 44 to the computer in the three dimensional optical sensor are not shown, and other wires such as those connecting the computer in the sensor to the main computer 38, and the connection between the main computer and the monitor 40 are not shown in detail to avoid confusion in the drawings, and it will be understood that such wires (or cables) are conventional in nature, and therefore do not need detailed disclosure.

Figure 4:
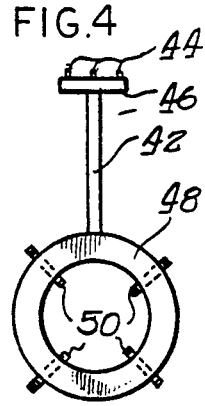
FIG. 4 is a front view of one form of orthopaedic marker.

Various means may be provided to secure the orthopaedic markers 42 to bones. As shown in FIG. 4 an orthopaedic marker 42 is provided at its outer end or head with a cross member 46 on which four LED's 44 are mounted. The four LED's 44 are independently energized, and are illuminated in sequence, rather than simultaneously. At the lower end of the orthopaedic marker 42, which comprises mainly a staff or post, there is a ring 48 having inwardly directed set screws 50 illustrated as four in number, although greater or lesser numbers could be used. This type of mounting structure would be used with finger bones, for example, or bones having an artificial joint substituted, which joint is separable. The set screws are turned in to engage against the bone for the surgical procedure, and then are retracted after the procedure so that the ring 48 and the orthopaedic marker may be withdrawn from the bone.

Figure 4A:
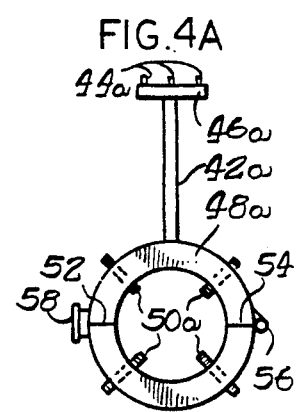
FIG. 4a is a view similar to FIG. 4 showing a modification.

A modification of the orthopaedic marker of FIG. 4 is shown in FIG. 4A, with parts being the same and identified by the use of similar numerals with the addition of the suffix a. The distinction in FIG. 4A is that the ring is split diametrically at 52 and 54, with a hinge 56 being connected across the split 54, and a suitable latch 58 being connected across the split 52. The orthopaedic marker of FIG. 4A is more readily installed and removed with regard to a larger number of bones by virtue of the fact that the ring 48a can be pivoted open and closed.

Figure 5:
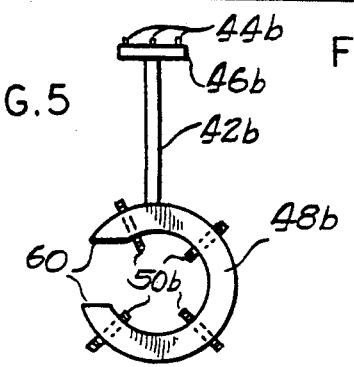
FIG. 5 is a similar view showing a further modified orthopaedic marker.

A further embodiment of the orthopaedic marker is shown in FIG. 5. Both parts are again similar, and are identified by like numerals with the addition of the suffix b. The distinction in this instance is that the ring 48b is open at 60 over a substantial arcuate extent. Thus, the ring 48b can be slipped over a bone by movement of the ring generally in a radial direction, following which the set screws 50b are screwed in to clamp the bone.

Figure 6:
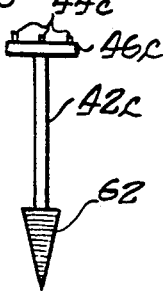
FIG. 6 is a generally similar view of a further modification of the orthopaedic marker.

Another modification of the orthopaedic marker is shown in FIG. 6. Many parts are the same, and are identified by similar numerals with the addition of the suffix c. In this instance there is no ring at the bottom or lower end of the staff or post. Instead, there is a tapered screw 62. A pilot hole would be bored in the bone, and the screw thread 62 threaded in to form a tight fit.

Figure 7:
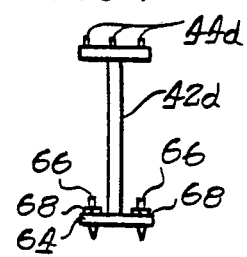
FIG. 7 is another similar view showing yet another modification of the orthopaedic marker.

Yet another embodiment of the orthopaedic marker is illustrated in FIG. 7. In this case there are similar parts that are identified by like numerals with the addition of the suffix d. In this instance the shaft or post is provided at the bottom end with a cross member 64. Small screws 66 are threaded through this member, and have tapered tips to screw into pilot holes drilled in the bone. Nuts 68 are provided for securing the screws in adjusted position.

Two adjacent bones 70 and 72 are shown in FIG. 3 arranged generally end to end, but without any specific coupling therebetween. These could be two adjacent arm bones with a joint therebetween, but this is not especially important, since the principal purpose of FIG. 3 is to show alignment of the bones. The leftmost bone 70 has a pair of orthopaedic markers 42 secured thereto. The securement can be by any of the structures shown in FIG. 4 through FIG. 7 or any other suitable structure. For example, this could be a structure similar to that in FIG. 5, but with the open space 60 opposite to the shaft or post 42b, rather than off to the side thereof. In any event, there are two markers 42 secured to the left bone 70, and there are two markers 42 secured to the right bone 72. Each orthopaedic marker is illustrated as having a single LED 44 at the outer end thereof, but there could be three, or any other suitable number. The LED's are switched on in sequence, so that in any given time only one LED is illuminated. This is controlled by a switching device in the three dimensional infrared optical sensor 32. Thus, there is no confusion as to what the "cameras" or individual sensor units are observing, whereby an accurate signal is sent out on the wire or cable illustrated leading to the computer 38, the computer being connected in turn to the monitor 40. The image shown on the monitor indicates the position of the four LED's and of the angular relationship thereof. Accordingly, the surgeon can compare the image before orthopaedic surgery, the image being stored in the computer, with the image after surgery to be sure that there is coincidence, whereby the bones are in the same positions following surgery, as before surgery.

A hip joint replacement is shown somewhat schematically in FIGS. 8-10. A human pelvis 74 has a right femur pivotally connected thereto by a normal hip joint 78, and a left femur 80 connected thereto by a normal hip joint 82. In this case the "normal" hip joint is intended to mean the original hip joint, whether it is in good operative condition, or deteriorated. In this case, it must be assumed that the right hip joint 78 has become deteriorated, and must be replaced. Accordingly, a pair or orthopaedic markers 42 with their LED's 44 are secured to the pelvis by any suitable means. For example, there could be an open ring similar to that in FIG. 5, but with the opening at the side opposite the shaft or post, rather than laterally thereof. Similarly, two additional orthopaedic markers 42 are secured to the femur in like manner. Each orthopaedic marker is shown as having a single LED 44, but more could be employed if desired.

The right femur 76 is shown detached in FIG. 4 with a ball 84 of bony material at the upper end thereof which is normally received in a socket in the pelvis. However, upon deterioration of the ball 84, or of the socket, or both, a replacement joint may be necessary. This is shown in FIG. 10. The upper end of the femur 76 is cut off, and a threaded shaft 86 is screwed therein. The shaft has an offset at 88, and carries at its upper end a spherical ball 90. The shaft and ball are preferably made of a suitable metal, such as stainless steel. A cavity 92 is surgically formed in the right side of the pelvis, and a block 94 is adhesively secured in the recess. The block has a concavity 96 of spherical configuration, and receives the ball 90. The block 94 preferably is a plastic resin material, polyurethane being one suitable example. The surgeon can view on a monitor 40 the position of the LED's 44 as in FIG. 8 prior to surgery, and this information is stored in a computer. The subsequent position of the LED's 44 following the hip joint replacement as in FIG. 10 then can be viewed by the surgeon on a monitor 40. The positions should be substantially the same before and after to insure that the femur is properly oriented relative to the pelvis, for proper operation.

A preoperative positional relationship of bones should be obtained if at all possible. In joint replacements, as in the hip joint replacement procedure illustrated in FIGS. 8-10, the preoperative positional relationship of the bones is obtained as noted. The bone tissue must be exposed for the marker or markers to be attached on either side of the future separation. For example, in the hip joint replacement illustrated, one or markers are attached to the patient's pelvis and to the femur below the point of separation. At this point the relationship of the femur to the pelvis can be established by collecting multiple points of data from all the markers by moving the joint through a range of motions.

The bones are severed in accordance with standard and established surgical practice. The head of the femur is removed in a hip joint replacement, the pelvis is repaired and the hip joint prosthesis is fitted. Any additional procedures are performed as required.

During a fitting or "setting" process, multiple sets of data are collected from the markers attached to the bones, and displayed on the monitor in several formats. For example, the current position and orientation of the bones can be displayed numerically in the standard 6-dimensional format $X,Y,Z,\alpha,\beta,\Omega$, alongside of the original baseline position and orientation collected preoperatively (and stored in the computer). Any differences are noted and displayed in order to guide the surgeon to the correct position and orientation. In addition to the above output, the data can be displayed graphically in order to enhance visualization.

Before the final mechanical attachment is performed, the data should be collected again in order to make sure that an acceptably small position and orientation error is present. After the attachment, the data should be checked again. At this point the markers are removed, and the surgical procedure is completed.

It has been noted heretofore that the individual position sensing units are not "cameras" in the traditional sense. The output of each is not an electronic representation of a two-dimensional image, such as is the case with video or television cameras. In reality, each sensor is designed to "look at" and "see" a single bright spot of light in the infrared frequency spectrum, and to output two position data proportional to the position (X,Y) of the spot in its rectangular point of view.

Each position sensor is capable of looking at only a single point of infrared light at a given time. A central synchronization circuit in the sensor 32 turns on each of the infrared light emitting diodes in sequence, such that only a single LED is turned on at any one time. Each LED stays on for a short period of time, for example one millisecond. After this time, the LED is turned off, and the subsequent LED is turned on, etc. This process continues indefinitely. As each LED is turned on by the synchronization circuit, the later causes each of the three positions sensors to output the LED's position as X,Y in its respective field of view. Since the synchronization circuit controls both the LED's and the position sensors, there can be no ambiguity about which LED is being viewed by the position sensors. This is a fundamental distinction from systems which are forced to distinguish among many simultaneously visible point light sources.

As described above, the X,Y positions of each sequentially strobed LED are obtained from all three position sensors. At this time, these positions are in the two-dimensional coordinate system of the respective position sensors. In order to improve the accuracy of the position measurement process, multiple readings of each LED are taken by both position sensors. Multiple readings are then averaged to filter out noise. Outlying data points with excessive standard deviation can be additionally discarded in order to improve the signal-to-noise ratio.

Because the three position sensors are viewing the same thing from different angle, it is now possible to compute the X,Y,Z position of each of the LED's.

From the foregoing it can be seen that bones can be very highly accurately returned to original position following orthopaedic surgery without having to rely so intensively on the skilled eye of the orthopaedic surgeon as has been necessary to date. The position following surgery can be compared quite precisely with the relative position of the bones prior to surgery, whereby there is no error in positioning as a result of the surgery.

The specific examples of the invention as herein shown and described are for illustrative purposes only. Various changes in structure will occur to those skilled in the art, and will be understood as forming a part of the present invention insofar as they fall within the spirit and scope of the appended claims.

The invention is claimed as follows:

1. Apparatus for precision bone alignment comprising a plurality of orthopaedic markers having means adapted for direct and fixed securement respectively to a plurality of bone portions to be aligned, each of said markers including a radiation emitting device thereon, radiation reception sensor means for detecting radiation emitted from said radiation emitting devices, means interconnected with said radiation emitting devices for sequentially causing said radiation emitting devices to emit radiation for a limited time, said devices otherwise not emitting radiation, said radiation reception sensor means outputting signals corresponding to positions of said radiation emitting devices, computer means connected to said sensor means for receiving said signals, and a monitor connected to said computer means for providing a visual display corresponding to the positions of said radiation emitting devices.

2. Apparatus as set forth in claim 1 wherein the means adapted for direct and fixed securement includes means adapted to release said markers from said securement.

3. Apparatus as set forth in claim 1 wherein said radiation emitting devices comprise light emitting diodes.

4. Apparatus as set forth in claim 3 wherein said light emitting diodes are infrared light emitting diodes.

5. Apparatus as set forth in claim 1 wherein said sensor means comprises three-dimensional sensor means outputting signals corresponding to three-dimensional positions of said radiation emitting devices.

6. Apparatus as set forth in claim 5 wherein said three-dimensional sensor means comprises a plurality of light sensors.

7. Apparatus as set forth in claim 6 wherein each sensor provides an analog signal corresponding to the positions of said radiation emitting devices.

8. Apparatus as set forth in claim 7 wherein the monitor displays in coordinates of X,Y,Z and $\alpha,\beta,\Omega$ for three-dimensional viewing.

9. Apparatus as set forth in claim 5 wherein the radiation emitting devices comprise light emitting diodes.

10. Apparatus as set forth in claim 9 wherein said radiation emitting devices comprise infrared light emitting diodes.

11. Apparatus as set forth in claim 5 and further including means for storing said signals prior to an orthopaedic/surgical procedure, and means for comparing signals after an orthopaedic/surgical procedure with the stored signals.

12. Apparatus as set forth in claim 1 wherein each marker includes means spacing a respective radiation emitting device outwardly away from a respective bone portion.

13. A method for precision bone alignment which comprises securing markers directly and fixedly to bone portions to be aligned, optically sensing a position of each of said markers, providing electrical signals corresponding to the positions sensed, electrically connecting said electrical signals to a monitor to provide a visual display corresponding to the positions of said markers, and manipulating said bone portions while observing said display to attain optical indication of alignment of said bone portions on said monitor.

14. A method as set forth in claim 13 which comprises sensing the positions of each of said markers with three-dimensional sensing means to provide three-dimensional electrical signals for a three-dimensional display.

15. A method as set forth in claim 13 including providing radiation emitting devices on said markers, sequentially activating said radiation emitting devices, and sensing the position of said radiation emitting devices when activated.

16. A method as set forth in claim 15 and further including providing a three-dimensional sensing means comprising a plurality of sensors to provide a plurality of electrical signals for a three-dimensional display on said monitor.

17. A method for precision bone alignment which comprises securing markers to bone portions to be aligned, optically sensing the position of each of said markers, providing electrical signals corresponding to the positions sensed, electrically connecting said electrical signals to a monitor to provide a visual display corresponding to the positions of said markers, retaining signals of the marker positions before an orthopaedic/surgical procedure, detecting the positions of said markers after said orthopaedic/surgical procedure, and comparing the positions of said markers before and after said orthopaedic/surgical procedure.

* * * * *